(12) United States Patent
Zimmermann

(10) Patent No.: US 7,427,503 B2
(45) Date of Patent: Sep. 23, 2008

(54) METHOD FOR TRANSFERRING MATERIAL IN A CELL SYSTEM

(75) Inventor: Ulrich Zimmermann, Waldbrunn (DE)

(73) Assignee: Eppendorf AG, Hamburg (DE)

( * ) Notice: Subject to any disclaimer, the term of this patent is extended or adjusted under 35 U.S.C. 154(b) by 441 days.

(21) Appl. No.: 10/220,374

(22) PCT Filed: Feb. 28, 2001

(86) PCT No.: PCT/EP01/02252

§ 371 (c)(1),
(2), (4) Date: Dec. 13, 2002

(87) PCT Pub. No.: WO01/66694

PCT Pub. Date: Sep. 13, 2001

(65) Prior Publication Data

US 2003/0148523 A1 Aug. 7, 2003

(30) Foreign Application Priority Data

Mar. 6, 2000 (DE) .............................. 100 10 959

(51) Int. Cl.
C12N 15/00 (2006.01)
C12N 15/01 (2006.01)
C12N 15/02 (2006.01)
C12N 15/03 (2006.01)
C12N 15/05 (2006.01)
C12N 15/06 (2006.01)
A61K 31/70 (2006.01)

(52) U.S. Cl. ................. 435/450; 435/455; 435/461; 435/468; 435/470; 435/471; 514/2; 514/44

(58) Field of Classification Search ............. 435/455, 435/460, 461, 441, 173.1, 173.4, 173.5, 173.6
See application file for complete search history.

(56) References Cited

U.S. PATENT DOCUMENTS

| 5,460,831 | A | | 10/1995 | Kossovsky et al. |
| 6,028,183 | A | * | 2/2000 | Lin et al. .................. 536/22.1 |
| 6,221,575 | B1 | * | 4/2001 | Roser et al. .................. 435/2 |
| 6,368,784 | B1 | * | 4/2002 | Murray ...................... 435/1.3 |
| 6,534,279 | B1 | * | 3/2003 | Agthoven et al. .......... 435/7.21 |
| 6,743,779 | B1 | * | 6/2004 | Unger et al. ................. 514/44 |
| 2003/0087820 | A1 | * | 5/2003 | Young et al. ................. 514/12 |
| 2006/0024358 | A1 | * | 2/2006 | Santini et al. ............... 424/448 |

FOREIGN PATENT DOCUMENTS

| WO | 96/20732 A2 | 7/1996 |
| WO | 00/09732 A1 | 2/2000 |
| WO | 00/15032 A1 | 3/2000 |
| WO | 00/22147 A1 | 4/2000 |

OTHER PUBLICATIONS

Golzio et al, Control by Osmotic Pressure of Voltage-Induced Permeabilziation and Gene Transfer in Mammalian Cells, Biophys Journal, 1998, vol. 74, p. 3015-3022.*

Tieleman, D.P., The molecular basis of electroporation, BMC Biocemistry, 2004, vol. 5(10), pp. 1-12.*

Ohse et al, Effects of Plasmid DNA Sizes and Several Other Factors on Transformation of *Bacillus subtilis* ISW1214 with Plasmid DNA by Electroporation, Biosc. Biotech, Biochem, 1995, 59 (8), pp. 1433-1437.*

Eroglu et al., "Intracellular trehalose improves the survival of cryopreserved mammalian cells", *Nature Biotechnology*, vol. 18, pp. 163-166 (Feb. 2000).

* cited by examiner

*Primary Examiner*—Maria B Marvich
(74) *Attorney, Agent, or Firm*—Caesar, Rivise, Bernstein, Cohen & Pokotilow, Ltd.

(57) ABSTRACT

Described is a method for method for transferring material through the membrane of at least one cell, wherein the transfer is carried out in the presence of trehalose. This method is applicable in particular in the field of genetic engineering and biotechnology.

9 Claims, 4 Drawing Sheets

METHOD FOR TRANSFERRING MATERIAL IN A CELL SYSTEM

Figure 1:
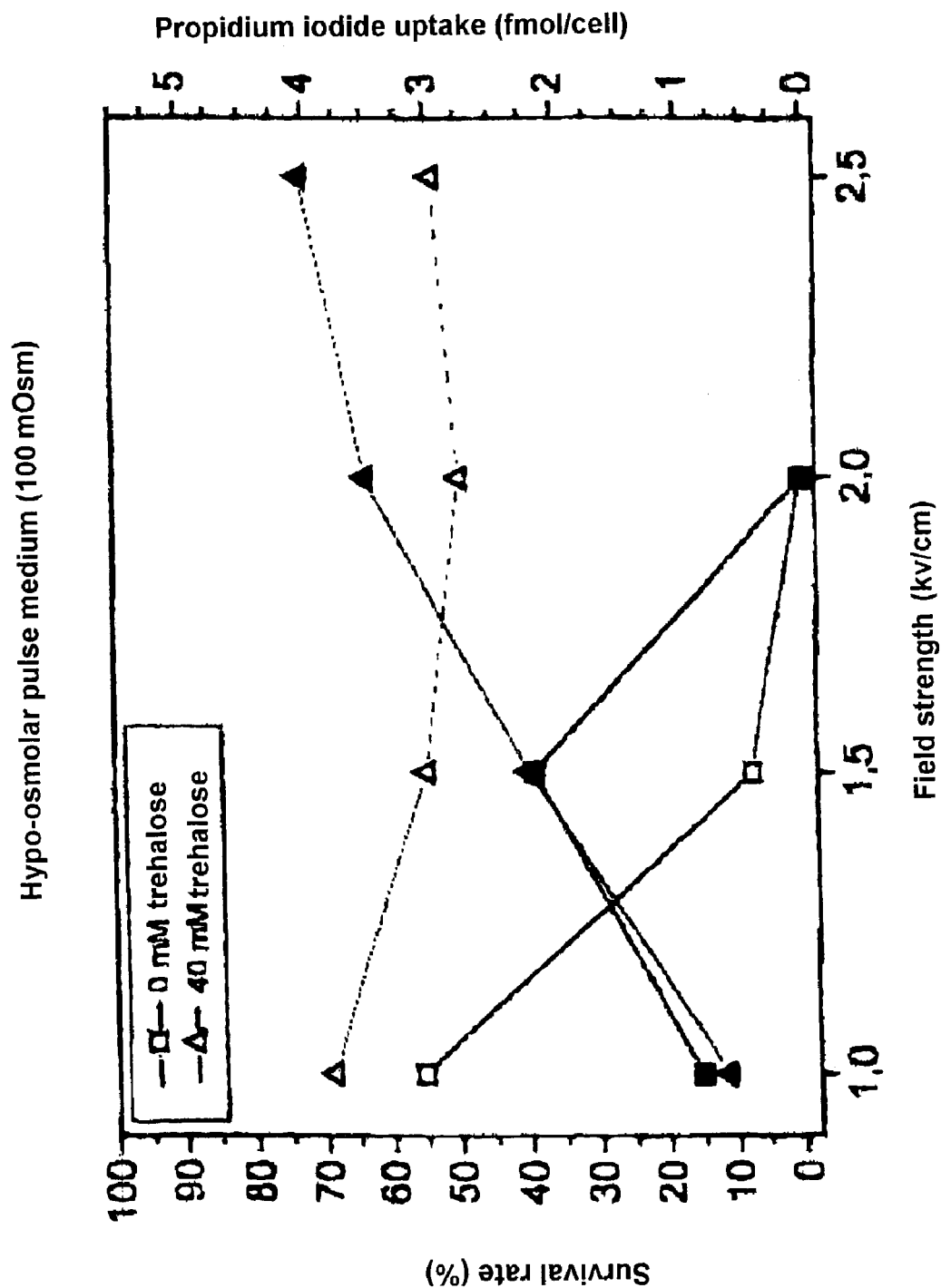

The present invention relates to a method for transferring material through the membrane of at least one cell, as well as to the application of this method in genetic engineering, biotechnology and hybridoma technology.

Over the past few years, methods for transferring biological materials through the membrane of a cell have increasingly gained in importance. In these methods, membrane-impermeable molecules are transferred through pores that have formed in the membrane as a result of extraneous forces. These methods are associated with a decisive advantage in that there is no need for the use of any vehicles.

Reversible membrane permeabilization through an electrical field, or alternatively, electroporation, has for some time been an established method of taking up free DNA, for example in eukaryotes. In this process, eukaryotes, in the presence of DNA, are exposed to a high-strength electrical field. However, only very little is known about the mechanism of DNA uptake during electroporation. It is generally assumed that due to the electric shock, pores form temporarily in the cell membrane, and the DNA, after contact with the lipid bi-layer of the cell membrane, is taken up into the cell.

While in electroporation, material is imported to the cell from the exterior, electrofusion differs in that at least two cells fuse. Electrofusion takes place by means of electrical pulses in two stages. In the first step, the cells to be fused are subjected to an alternating electrical field in which they are mutually attracted to each other as a result of dielectrophoresis. Conductivity of the medium should be as low as possible. In the second step, electrofusion is triggered by very short electrical direct-current pulses. This leads to interaction of membrane parts which leads to fusion. With this method it is possible, for example, to fuse protoplasts. It is also possible to produce hybrids of animal cells, such as hybridoma cells, as well as yeasts.

It has thus been known for some time to cause transfer of material into a cell in that the cells are subjected to irradiation treatment for the purpose of permeabilization. In this process, the cells are for example subjected to laser irradiation, after which the material can then diffuse through the cell membrane.

Methods have thus already been used in which, for the purpose of permeabilization, the membranes of cells are treated with chemical substances. Such substances include pore-forming and/or diffusion-promoting peptide antibiotics and depsipeptide antibiotics, such as valinomycin, and detergents, such as sodium dodecyl sulfate.

The methods described above are based on the following fundamental principle: local apertures in the cell membrane result from energy-intensive electrical, electromagnetic, or mechanical forces such as current pulses, irradiation, ultrasound and pressure, and chemical treatment. Submicroscopic holes or pores occur to form. Such treatment makes possible introducing the biological material from the exterior, or, between cells, if two cells are to be fused. After diminished intensity of these forces acting from the exterior, the pores in the membrane close up, and the material remains in the cell.

However, it has been shown that in this method, the fraction of surviving cells, i.e. intact cells which have been reversibly permeabilized, is often exceeded by the fraction of dead cells. This is due to the permeabilized cells being unable to completely re-close the pores after a reduction in the intensity of the external forces. This then leads to the loss of important cell functions so that the cell is no longer able to maintain its metabolism, a situation which finally leads to the death of the cell. For this reason, it was quite normal in the method according to the state of the art, to have to accept a fraction of dead cells, a factor which had a significant negative effect on the efficiency of this method.

It is thus the object of the present invention to provide a method for transferring material through the membranes of cells, by which a high degree of reversibly permeabilized, so-called surviving cells is achieved, and thus the fraction of dead cells is drastically reduced. An increase in the fraction of surviving cells should also be realized in the event of working with more stringent reaction conditions, for example increased field strengths.

This object is solved by the method according to claim 1. The sub-claims relate to preferred embodiments of the method according to the invention.

Furthermore, the claims describe particular applications of the method according to the invention.

The present invention relates to a method for transferring material through the membrane of at least one cell, in an aqueous medium which is characterized in that the transfer is carried out in the presence of trehalose.

Figure 2:
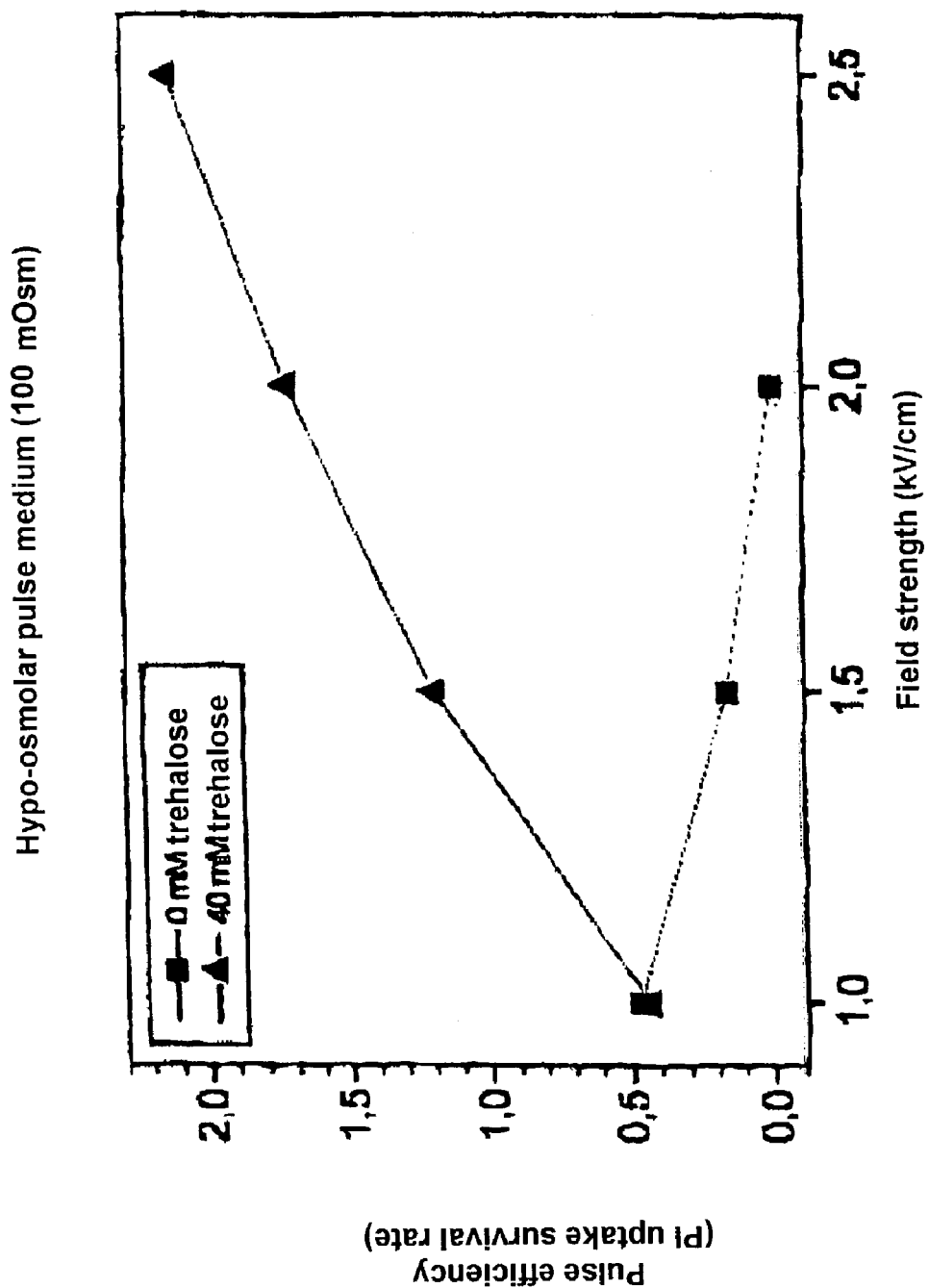
Figure 3:
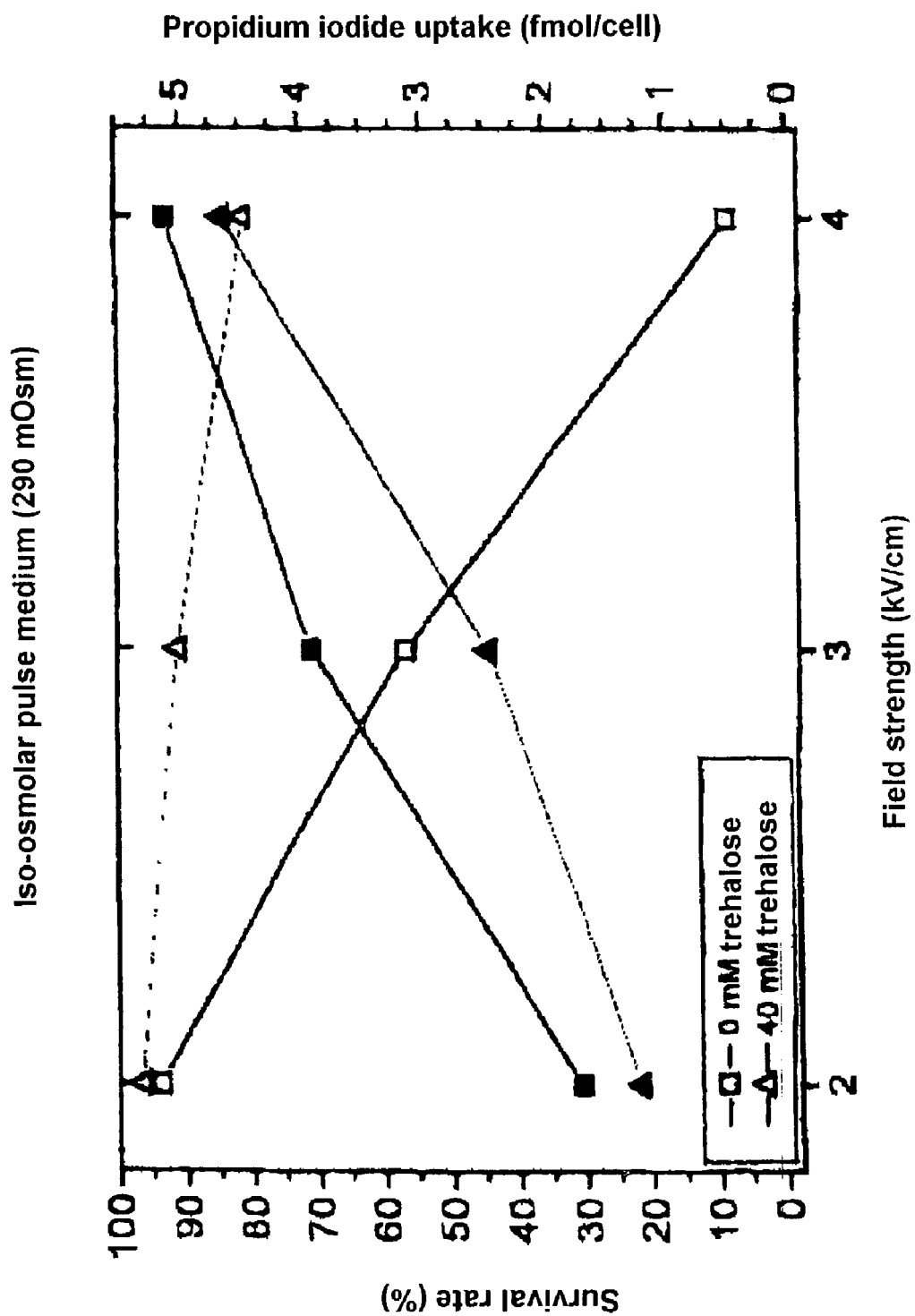
Figure 4:
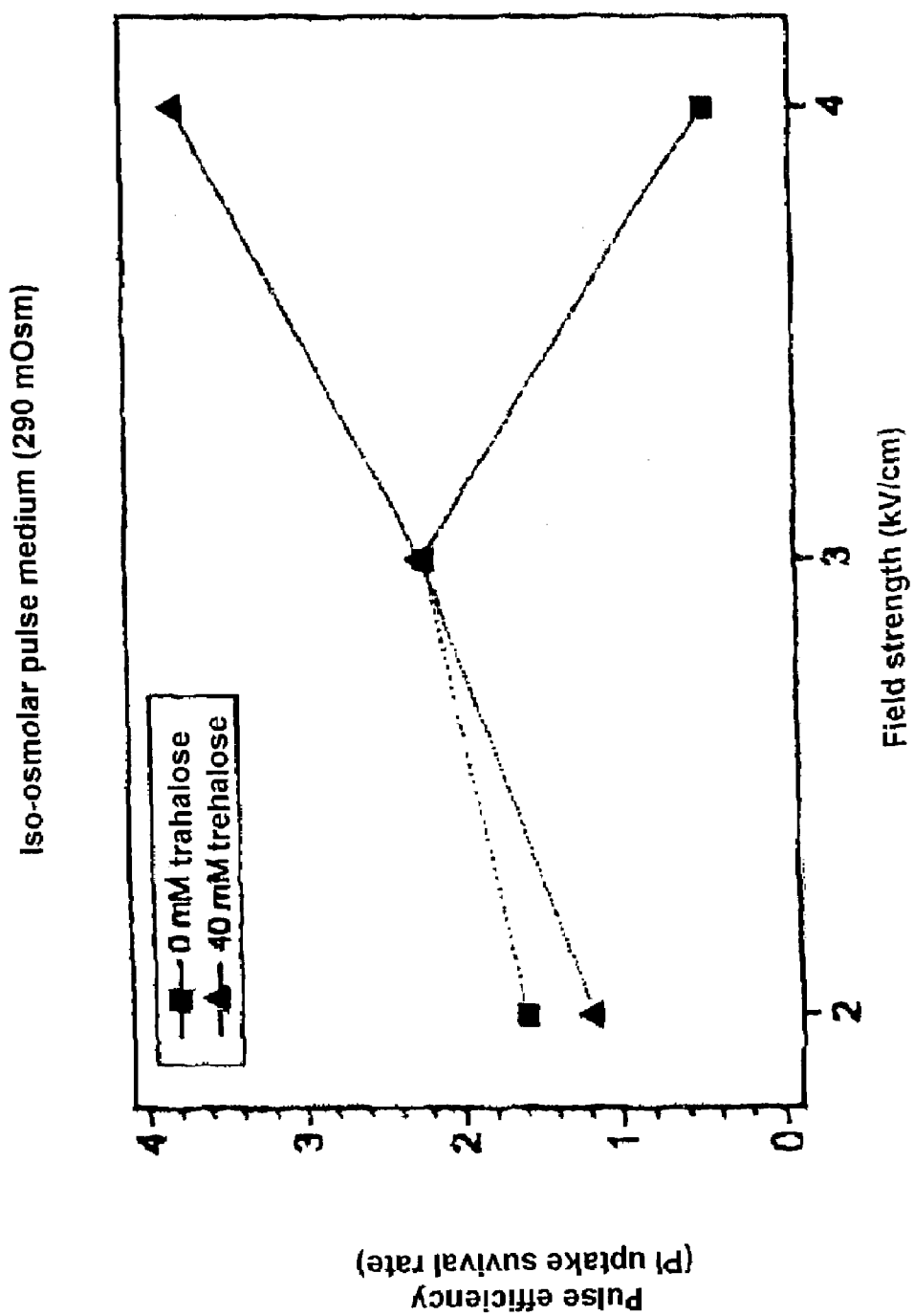

The method according to the invention is explained in more detail with reference to the accompanying figures. The following are shown:

FIG. 1—a graphic representation showing the propidium iodide uptake and the survival rate (% reversibly permeabilized cells) depending on the field strength in the hypo-osmolar medium;

FIG. 2—a graphic representation showing the "pulse efficiency" as a measure of the yield, depending on the field strength in the hypo-osmolar medium;

FIG. 3—a graphic representation showing the propidium iodide uptake and the survival rate (% reversibly permeabilized cells) depending on the field strength in the iso-osmolar medium; and FIG. 4—a graphic representation showing the "pulse efficiency" as a measure of the yield, depending on the field strength in the iso-osmolar medium.

According to the invention it has been shown that the survival rate of reversibly permeabilized cells is drastically increased if trehalose is added to the aqueous working medium. Presumably, the trehalose has a membrane-stabilizing and membrane-healing effect after the closure of the pores following introduction of the biological material. Consequently, the permeabilized cells survive and there is thus no danger of cell functions dying due to the loss of cell fluids and cell organelles.

The use of trehalose in methods of the type described here has not been known up to now. The literature merely indicates that trehalose makes a contribution to the cryoconservation of mammalian cells (Nature Biotechnology, vol. 18, February 2000) and to sustaining intact human cells without the presence of water (Nature Biotechnology, vol. 18, February 2000).

In principle, any trehalose which is dissolved in the respective working buffers is suitable. Trehalose is a disaccharide which occurs naturally; in one case it is also made synthetically. $\alpha,\alpha$-trehalose is the best-known trehalose and the one that most frequently occurs naturally. $\alpha,\beta$-trehalose also occurs naturally; it has been found to be present in honey. $\beta,\beta$-trehalose is only available synthetically. Preferably, $\alpha,\alpha$-trehalose is added to the working buffer for transferring material.

The method according to the invention is preferably suitable for the transfer of material in which at least one cell is involved which is reversibly permeabilized, or in which at least two cells which adhere to each other are involved which are permeabilized and which practically exchange material between each other. In this case it is possible that at least two cells fuse. There is also a further variant where several cells fuse, quasi by forming a string of pearls.

Normally, transfer of material into the cell is through a local aperture or apertures in the membrane of the cell or the cells. This is called permeabilization of the membrane. Presumably material is transferred through part of the apertures while the other part of the apertures remains without material passage. Having taken up the material, these apertures too, have to close. It is especially in the context of this process that trehalose has proven to be particularly advantageous as a membrane-healing additive.

As a rule, permeabilization of the membrane can take place by applying an electrical field, by irradiation, or by chemical treatment. The actual method selected essentially depends on the type of cells to be transformed and the type of material to be transferred.

Methods including electrotransfection, electroporation, or electrofusion, either in macroscopic devices or in microsystems/microstructures, are suitable for electrical permeabilization. These are established methods which have been successfully in use for some years in gene technology. In particular in the case of electroporation it is often necessary to work with high field strengths. However, this has traditionally been associated with a problem in that the cells subsequently died, i.e. that they had been irreversibly permeabilized. This led to considerable reductions in yield. However, if, according to the invention, trehalose is added to the electroporation buffer, it is possible to obtain reversibly permeabilized living cells, even at high field strengths. This factor renders the method according to the invention far more economical.

Thus, permeabilization by way of UV irradiation or laser irradiation is also possible. This type of irradiation is advantageous when due to the cells used and due to the material to be transferred, electrical treatment is not indicated.

Thus, chemical treatment for permeabilization is recommended only when it is not advisable to carry out transfer in the electrical field or transfer by way of irradiation. If chemical treatment is to be used, then, for permeabilization, the cells are to be treated with antibiotics, detergents, etc.

With the method according to the invention, any suitable biological materials can be transferred, including: xenomolecules, DNA and RNA, plasmids, chromosomes, parts of chromosomes as well as artificial chromosomes, proteins and glycoproteins, cells, parts of cells, and cell organelles, or low-molecular foreign matters.

The biological material can be trehalose or a trehalose/saccharose mixture. In this way it is possible to introduce trehalose or the trehalose/saccharose mixture as an intracellular cryoprotectant or protectant against desiccation.

As far as the cells used during transfer are concerned, the method according to the invention is not subject to any limitations. It is possible to use natural cells or membrane-enveloped vesicles for the transfer of material. Natural or artificial vesicles, liposomes and micelles are examples of membrane-enveloped vesicles.

In the case of natural cells, according to the invention it is possible to permeabilize and transform prokaryotic and eukaryotic cells. Bacteria, blue algae and archae-bacteria are examples of prokaryotic cells. Eukaryotic cells can have their origins in protozoa, plants (including algae), fungi (including yeasts), animals or humans.

For electroporation and electrofusion, it is possible to work in the iso-osmolar medium or in the hypo-osmolar medium. In animal cells, the hypo-osmolar medium has an osmolarity of 75 to 250 mOsm and is thus nonphysiological. The osmolarity of an iso-osmolar medium is approx. 300 mOsm, with the medium corresponding to the physiological environment. In contrast, in the case of plant cells, the osmolarity of an iso-osmolar medium is approx. 500 mOsm. The hypo-osmolar medium ranges from approx. 400 to 450 mOsm.

It has been found that the protective effect of trehalose becomes evident in particular in the hypo-osmolar medium.

It has been shown-that the concentration of trehalose in an aqueous medium, for example in the case of electrical treatment, should be within the range of 1 to 200 mM. It has been found that trehalose increases the fraction of surviving cells after pulse application, with optimal yield occurring at approx. 30 to 50 mM which is not increased by further increasing the concentration level. Therefore, a concentration range of approximately 30 to 50 mM is preferred for pulse application.

It has been shown that a further embodiment of the method according to the invention brings about increased yield of reversibly permeabilized cells even if a mixture of trehalose and saccharose is added to the working buffer. The ratio of trehalose to saccharose ranges from 1:2 to 1:10. The concentration in the mixture ranges from 200 to 300 mM.

The present method is eminently suitable for introducing biological material into a cell, or for transfer between at least two cells. The method can therefore be applied in practically all areas of biotechnology, genetic engineering and microsystem technology. In particular, it is especially suited to hybridoma technology, for example where elecrofusion is used. Furthermore, plant protoplasts can easily be fused with the method according to the invention.

As a result of the presence of trehalose in the working medium, the method according to the invention has many advantages. These are due to the fact that trehalose has a protective effect on the cells to be treated. Trehalose stabilizes the cell membrane and causes fast healing of the pores, for example following the uptake of foreign material and weakening of the external forces. In particular in the case of electroporation it has been found that the protective effect of trehalose is very pronounced at high field strengths, while at the same time hardly being affected by the pulse duration. It has been shown that the protective effect of trehalose is stronger in the hypotonic pulse medium than it is in the isotonic pulse medium. The effect of trehalose is somewhat more pronounced in a poorly conductive medium than it is in a stronger conducting medium. These advantageous protective properties of trehalose are in particular highly beneficial if work is carried out at stringent pulse conditions, such as poor conductivity, hypotonic stress, or high field strength.

Below, the method according to the invention is explained in more detail by means of examples.

EXAMPLES

Example 1

Electroporation of Cells with and without Trehalose in a Hypo-osmolar Working Medium.

A phosphate buffer with 1.15 mM $K_2HPO_4/KH_2PO_4$ buffer, pH 7.2, was used as a pulse medium. KCl at a concentration of 10 mM ($\alpha$=1.5–1.6 mS/cm) was added as a conducting salt. After this, trehalose at the respective concentration was added to the pulse medium. Osmolarity was adjusted to 100 mOsm by the addition of inositol, so as to obtain a hypo-osmolar solution.

Jurkat cells that are cells of a human T-lymphocytes line were used. 40 μg/ml propidium iodide, which is a membrane-impermeable DNA dye, was added as the material to be transferred.

Pulse application took place after 10 minutes of incubation prior to pulse application, in the pulse medium at room temperature (cell density: $2-3 \times 10^6$ cells/ml). Pulse duration was 20 μs.

Electroporation took place in an Eppendorf multiporator. After pulse application, the pores were left to reseal for 10 min at room temperature.

Electropermeabilisation took place at the following trehalose concentrations: 0 mM and 40 mM (α,α-trehalose).

Pulsing takes place at 4° C. or at room temperature. This can be single pulsing; however, multiple pulsing involving up to 3 pulses can at times be advantageous.

The results are shown in FIGS. 1 and 2.

FIG. 1 diagrammatically shows the uptake of propidium iodide or the survival rate of the electropermeabilized cells depending on the field strength. Poration without trehalose is shown by squares. Preparation with 40 mM Trehalose is shown by triangles. Outline symbols designate the survival rate (percentage of reversibly-permeabilized cells) while solid symbols designate the propidium iodide uptake into the cell.

As shown in FIG. 1, in a pulse medium without trehalose, cells sustain irreversible damage at field strengths from 1.5 kV/cm onwards, and die-off as a result of loss of cell functions (outline squares). In contrast, in a pulse medium in 40 mM trehalose, there is only a relatively small percentage of dead cells (outline triangles), even at very high field strengths up to 2.5 kV/cm. This is an indication that the cells were reversibly permeabilized and have thus remained viable. Propidium iodide uptake is only slightly influenced by trehalose.

FIG. 2 depicts an investigation of the pulse efficiency which represents the product of propidium iodide uptake and survival rate, as a measure of the yield obtained from electroporation, depending on the field strength. It is evident that with 40 mM trehalose in the pulse medium (triangles), these values rise rapidly as the field strength increases, and are significantly above the values of a control sample (squares) which was not treated with trehalose. This significant increase in yield is also due to a greatly improved survival rate in the presence of 40 mM trehalose.

Example 2

Electroporation of Cells with and without Trehalose in an Iso-osmolar Working Medium.

Essentially, the same experimental conditions as in Example 1 applied, except that the osmolarity of the pulse medium was adjusted to iso-osmolar conditions by adding inositol to 290 mOsm.

Again, α,α-trehalose was added in the following concentrations: 0 mM and 40 mM.

The results are shown in FIGS. 3 and 4.

FIG. 3 shows the dependence of the survival rate and the propidium iodide uptake in relation to the field strength. Outline symbols designate the survival rate, while solid symbols designate the propidium iodide uptake.

In the iso-molar pulse medium, the survival rate in the case of untreated cells (0 mM, outline squares) is many times less than in the case of cells treated with 40 mM trehalose (outline triangles), above all at high field strength. In contrast, propidium iodide uptake varies less markedly. It is important to note that from a field strength of 3 kV/cm onwards, there is a drastic die-off of cells if there is no trehalose in the pulse medium.

FIG. 4 shows the pulse efficiency dependent on the field strength for the present pulse media (0 to 40 mM trehalose). As the field strength increases, a gradual increase in the pulse efficiency is evident in the pulse medium containing trehalose (triangles), while without trehalose (squares) in the pulse medium at high field strength, a drastic reduction in yield is evident. Here again, trehalose displays its protective effect in stringent pulse conditions.

The invention claimed is:

1. A method for transferring a material selected from the group consisting of xenomolecules, DNA, RNA, plasmids, parts of chromosomes, proteins, and glycoproteins, through a membrane of at least one cell in an aqueous medium, said method comprising: permeabilizing the membrane by applying an electric field to create a permeabilized membrane; and allowing a transfer of the material through the permeabilized membrane in the aqueous medium, and wherein the aqueous medium comprises a concentration of 1-200 mM trehalose and is: (a) an iso-osmolar medium and the electric field has a strength of 3 to 4 kV/cm, or (b) a hypo-osmolar medium and the electric field has a strength of 1.5 to 2.5 kV/cm.

2. The method according to claim 1, wherein the transfer of the material comprises moving the material from an exterior of the at least one cell into an interior of the at least one cell, or wherein the material is transferred between at least two cells.

3. The method according to claim 1, wherein the material is obtained from a biological source.

4. The method according to claim 1, wherein the at least one cell is a living cell.

5. The method according to claim 4, wherein the at least one cell is at least one of a prokaryotic living cell and an eukaryotic living cell.

6. The method according to claim 5, wherein the eukaryotic living cell is of human, animal or plant origin.

7. The method according to claim 1, wherein the concentration of trehalose is 30 to 50 mM.

8. The method according to claim 1, wherein the material is obtained from a biological source, and the method is employed in a field selected from the group consisting of genetic engineering, biotechnology, hybridoma technology and microsystem technology.

9. The method according to claim 1, wherein the trehalose does not contribute to cryoconservation of the cell.

* * * * *